United States Patent
Tremblay-Darveau et al.

(10) Patent No.: US 12,148,068 B2
(45) Date of Patent: Nov. 19, 2024

(54) SYSTEMS AND METHODS FOR VASCULAR RENDERING

(71) Applicant: KONINKLIJKE PHILIPS N.V., Eindhoven (NL)

(72) Inventors: Charles Tremblay-Darveau, Seattle, WA (US); Paul Sheeran, Woodinville, WA (US); Thanasis Loupas, Kirkland, WA (US); Liang Zhang, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 17/908,341

(22) PCT Filed: Mar. 5, 2021

(86) PCT No.: PCT/EP2021/055539
§ 371 (c)(1),
(2) Date: Aug. 31, 2022

(87) PCT Pub. No.: WO2021/176030
PCT Pub. Date: Sep. 10, 2021

(65) Prior Publication Data
US 2023/0073704 A1 Mar. 9, 2023

Related U.S. Application Data

(60) Provisional application No. 62/986,023, filed on Mar. 6, 2020.

(51) Int. Cl.
| | |
|---|---|
| G09G 5/02 | (2006.01) |
| G06T 5/20 | (2006.01) |
| G06T 5/50 | (2006.01) |
| G06T 5/90 | (2024.01) |
| G06T 7/90 | (2017.01) |
| G06T 11/00 | (2006.01) |

(52) U.S. Cl.
CPC .............. G06T 11/001 (2013.01); G06T 5/20 (2013.01); G06T 5/50 (2013.01); G06T 5/90 (2024.01);
(Continued)

(58) Field of Classification Search
CPC . G09G 5/02; G09G 5/06; G09G 5/363; G06T 11/001; G06T 5/20;
(Continued)

(56) References Cited

U.S. PATENT DOCUMENTS

| | | | |
|---|---|---|---|
| 4,932,415 A | 6/1990 | Angelson et al. | |
| 5,855,556 A | 1/1999 | Shirai | |

(Continued)

FOREIGN PATENT DOCUMENTS

| | | |
|---|---|---|
| JP | H1014919 A | 1/1998 |
| JP | 2012245021 A | 12/2012 |

OTHER PUBLICATIONS

International Search Report and Written Opinion for PCT/EP2021/055539, Mailing date: Jun. 10, 2021, 13 pages.
(Continued)

Primary Examiner — Gordon G Liu

(57) ABSTRACT

In some examples, color Doppler data may be separated into luminance data and chrominance data. The luminance data may be modified without modifying the chrominance data. In some examples, the luminance data may be adjusted based, at least in part, on power Doppler data. The adjusted luminance data may be recombined with the chrominance data to provide augmented color Doppler data. In some examples, the power Doppler data may be enhanced by filtering, for example, by applying a Frangi vesselness filter, prior to being used to adjust the luminance data of the color Doppler data.

20 Claims, 5 Drawing Sheets

(52) U.S. Cl.
CPC ............ *G06T 7/90* (2017.01); *G06T 2200/24* (2013.01); *G06T 2207/10024* (2013.01); *G06T 2207/10132* (2013.01); *G06T 2207/20036* (2013.01); *G06T 2207/20212* (2013.01)

(58) Field of Classification Search
CPC . G06T 2207/10132; G06T 2207/20036; G06T 2207/20212; G06T 2207/10024; G06T 2200/24; G06T 7/90; G06T 5/90; G06T 5/50; G06F 3/04845
USPC ........................................................ 345/591
See application file for complete search history.

(56) References Cited

U.S. PATENT DOCUMENTS

| | | | |
|---|---|---|---|
| 6,176,828 B1 | 1/2001 | Becker et al. | |
| 6,443,896 B1 | 9/2002 | Detmer | |
| 6,530,885 B1 | 3/2003 | Entrekin et al. | |
| 7,532,254 B1* | 5/2009 | Woodall ................... | H04N 9/78 348/669 |
| 7,972,269 B2 | 7/2011 | Hayashi et al. | |
| 2006/0241461 A1 | 10/2006 | White et al. | |
| 2008/0208053 A1 | 8/2008 | Hashimoto | |
| 2010/0063398 A1 | 3/2010 | Halmann et al. | |
| 2010/0134629 A1* | 6/2010 | Lindop .................. | A61B 8/485 382/128 |
| 2020/0222018 A1* | 7/2020 | Van Walsum .......... | A61B 6/463 |

OTHER PUBLICATIONS

Muth, S. et al., "Unsupervised Dealiasing and Denoising of Color-Doppler Data", Medical Image Analysis, 2011, vol. 15, pp. 577-588.
Frangi, A.F. et al., " Multiscale Vessel Enhancement Filtering", Medical Image Computing and Computer-Assisted Intervention—MICCAI'98. MICCAI 1998; Lecture Notes in Computer Science, vol. 1496, pp. 130-137.

* cited by examiner

SYSTEMS AND METHODS FOR VASCULAR RENDERING

CROSS-REFERENCE TO PRIOR APPLICATIONS

This application is the U.S. National Phase application under 35 U.S.C. § 371 of International Application No. PCT/EP2021/055539, filed on Mar. 5, 2021, which claims the benefit of U.S. Provisional Patent Application No. 62/986,023, filed on Mar. 6, 2020. These applications are hereby incorporated by reference herein.

TECHNICAL FIELD

This application relates to rendering of vasculature in ultrasound imaging. More specifically, this application relates to rendering vasculature from Doppler data.

BACKGROUND

Doppler ultrasound is an ultrasound technique that detects blood flow by sampling repeatedly a region of interest at high pulse repetition frequency (PRF). Example PRFs include >200 Hz for power Doppler and kHz ranges for color Doppler. Motion is detected as a phase shift per PRF in the in-phase/quadrature echo signal (IQ) and scales proportionally with the axial velocity. Moving blood echoes can be separated from stationary tissue background by applying a high-pass filter along the slow time direction (e.g., wall filter). The autocorrelation (R) of the flow IQ signal is then typically computed and the power Doppler is extracted from zero-th lag (R0) while the color Doppler is estimated from the phase of the first lag (~arg[R1]).

Color Doppler provides quantitative information about the blood flow, including velocity and direction of flow, but provides limited vascular rendering capabilities. Power Doppler is typically more sensitive than color Doppler and provides better vascular rendering, but power Doppler provides less quantitative information than color Doppler. Accordingly, an improved technique for rendering blood vessels from color Doppler data is desired.

SUMMARY

Systems and methods for rendering vasculature from Doppler data are disclosed. In some examples, the luminance portion of the velocity color map from color Doppler data may be augmented. Color Doppler data (e.g., a red-green-blue (RGB) velocity color map) may be decomposed into its luminance and chrominance (e.g., chroma) channels. The luminance may be adjusted based, at least in part, on power Doppler data, while the chrominance is unaltered. The adjusted luminance may be recombined with the chrominance to generate augmented color Doppler data. In some applications, adjusting the luminance of the color Doppler based on the power Doppler may improve the rendering of vessels.

In accordance with at least one example disclosed herein, an ultrasound imaging system may include a processor configured to analyze ultrasound signals to generate power Doppler data and color Doppler data, separate the color Doppler data into luminance data and chrominance data, adjust the luminance data based, at least in part, on the power Doppler data to generate adjusted luminance data, and combine the adjusted luminance data and the chrominance data to generate augmented color Doppler data.

In accordance with at least one example disclosed herein, a method may include decomposing color Doppler data into luminance data and chrominance data, adjusting the luminance data based, at least in part, on power Doppler data to generate adjusted luminance data, and combining the adjusted luminance data and the chrominance data to generate augmented color Doppler data.

In accordance with at least one example disclosed herein, a non-transitory computer readable medium including instructions, that when executed, may cause an ultrasound imaging system to analyze ultrasound signals to generate power Doppler data and color Doppler data, separate the color Doppler data into luminance data and chrominance data, adjust the luminance data based, at least in part, on the power Doppler data to generate adjusted luminance data, and combine the adjusted luminance data and the chrominance data to generate augmented color Doppler data.

DESCRIPTION

Figure 1:
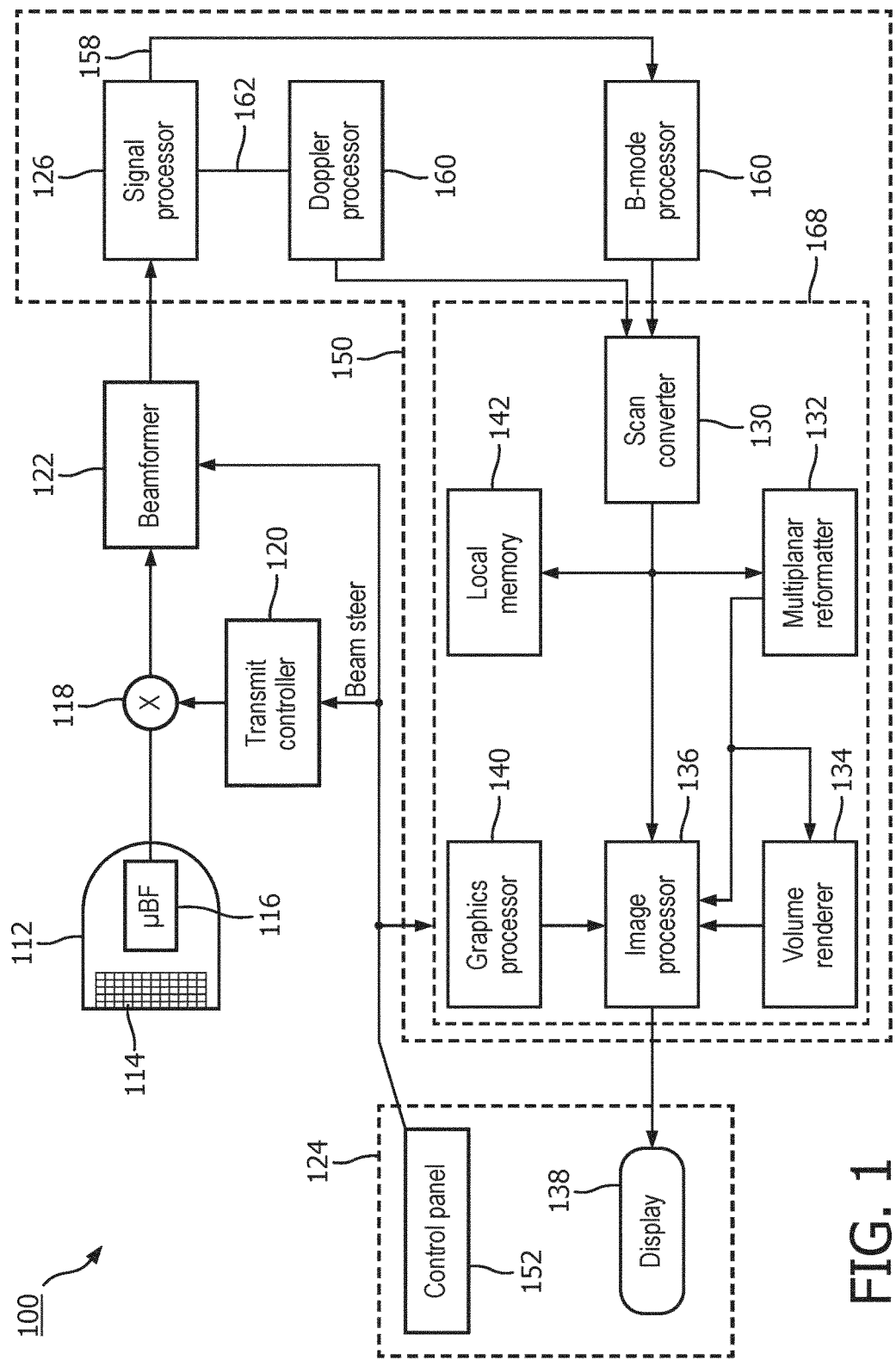
FIG. 1 is a block diagram of an ultrasound imaging system arranged in accordance with examples of the present disclosure.

The following description of certain exemplary examples is merely exemplary in nature and is in no way intended to limit the disclosure or its applications or uses. In the following detailed description of examples of the present systems and methods, reference is made to the accompanying drawings which form a part hereof, and in which are shown by way of illustration specific examples in which the described systems and methods may be practiced. These examples are described in sufficient detail to enable those skilled in the art to practice the presently disclosed systems and methods, and it is to be understood that other examples may be utilized and that structural and logical changes may be made without departing from the spirit and scope of the present disclosure. Moreover, for the purpose of clarity, detailed descriptions of certain features will not be discussed when they would be apparent to those with skill in the art so as not to obscure the description of the present disclosure. The following detailed description is therefore not to be taken in a limiting sense, and the scope of the present systems and methods is defined only by the appended claims.

As previously described, in Doppler ultrasound, the autocorrelation (R) of the flow in-phase/quadrature echo signal (IQ) signal is computed and the power Doppler is extracted from zero-th lag (R0) while the color Doppler is estimated from the phase of the first lag (~arg[R1]).

Color Doppler provides quantitative information about the blood flow, including velocity and direction of flow. The arg[R1] does not scale proportionally with respect to blood volume, which may limit blood vessel morphological rendering based on color Doppler data. The R0 of power Doppler scales proportionally with respect to blood volume, which is beneficial for morphological rendering. However, power Doppler provides less quantitative information than color Doppler because it is independent of angle, velocity, and direction.

Currently, to overcome the limitations of color Doppler, when blending a color Doppler image with an anatomical B-mode ultrasound image, the flow/tissue blend may be arbitrated by leveraging R0 of the power Doppler data. A fixed threshold is typically selected from an R0 receiver operating characteristic (ROC) curve to hide color pixels that may belong to noise. This process may improve the morphological rendering of blood vessels, but fine details of the vascular trees are lost. Furthermore, overshooting the ROC threshold reduces sensitivity while undershooting the ROC threshold causes the color Doppler signal to bleed over the blood vessel wall in the B-mode image. Thus, in some applications, it may be beneficial to have improved vessel rendering while maintaining the quantitative information provided by color Doppler.

According to examples of the present disclosure, color Doppler data may be decomposed into a luminance channel and a chrominance (also referred to as chroma) channels. The data of the luminance channel (e.g., the luminance data) may be adjusted (e.g., modified) based, at least in part, on power Doppler data. The adjusted data of the luminance channel may be recombined with the unaltered data of the chrominance channel to provide augmented color Doppler data. In some examples, the augmented color Doppler data may provide improved rendering of vessels. In some examples, the quantitative data regarding blood flow of the color Doppler data may be preserved in the augmented color Doppler data.

FIG. 1 shows a block diagram of an ultrasound imaging system 100 constructed in accordance with the principles of the present disclosure. An ultrasound imaging system 100 according to the present disclosure may include a transducer array 114, which may be included in an ultrasound probe 112, for example an external probe or an internal probe such as an intravascular ultrasound (IVUS) catheter probe. In other examples, the transducer array 114 may be in the form of a flexible array configured to be conformally applied to a surface of subject to be imaged (e.g., patient). The transducer array 114 is configured to transmit ultrasound signals (e.g., beams, waves) and receive echoes (e.g., received ultrasound signals) responsive to the transmitted ultrasound signals. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some examples, the transducer array 114 may be coupled to a microbeamformer 116, which may be located in the ultrasound probe 112, and which may control the transmission and reception of signals by the transducer elements in the array 114. In some examples, the microbeamformer 116 may control the transmission and reception of signals by active elements in the array 114 (e.g., an active subset of elements of the array that define the active aperture at any given time).

In some examples, the microbeamformer 116 may be coupled, e.g., by a probe cable or wirelessly, to a transmit/receive (T/R) switch 118, which switches between transmission and reception and protects the main beamformer 122 from high energy transmit signals. In some examples, for example in portable ultrasound systems, the T/R switch 118 and other elements in the system can be included in the ultrasound probe 112 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 114 under control of the microbeamformer 116 is directed by the transmit controller 120, which may be coupled to the T/R switch 118 and a main beamformer 122. The transmit controller 120 may control the direction in which beams are steered. Beams may be steered straight ahead from (orthogonal to) the transducer array 114, or at different angles for a wider field of view. The transmit controller 120 may also be coupled to a user interface 124 and receive input from the user's operation of a user input device (e.g., user control). The user interface 124 may include one or more input devices such as a control panel 152, which may include one or more mechanical controls (e.g., buttons, encoders, etc.), touch sensitive controls (e.g., a trackpad, a touchscreen, or the like), and/or other known input devices.

In some examples, the partially beamformed signals produced by the microbeamformer 116 may be coupled to a main beamformer 122 where partially beamformed signals from individual patches of transducer elements may be combined into a fully beamformed signal. In some examples, microbeamformer 116 is omitted. In these examples, the transducer array 114 is under the control of the main beamformer 122, and the main beamformer 122 performs all beamforming of signals. In examples with and without the microbeamformer 116, the beamformed signals of the main beamformer 122 are coupled to processing circuitry 150, which may include one or more processors (e.g., a signal processor 126, a B-mode processor 128, a Doppler processor 160, and one or more image generation and processing components 168) configured to produce an ultrasound image from the beamformed signals (i.e., beamformed RF data).

The signal processor 126 may be configured to process the received beamformed RF data in various ways, such as bandpass filtering, decimation, I and Q component separation, and harmonic signal separation. The signal processor 126 may also perform additional signal enhancement such as speckle reduction, signal compounding, and electronic noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 158 which couples the signals from the signal processor 126 to a B-mode processor 128 for producing B-mode image data.

The B-mode processor 128 can employ amplitude detection for the imaging of structures in the body. The B-mode processor 128 may generate signals for tissue images and/or contrast images. The signals produced by the B-mode processor 128 may be coupled to a scan converter 130 and/or a multiplanar reformatter 132. The scan converter 130 may be configured to arrange the echo signals from the spatial relationship in which they were received to a desired image format. For instance, the scan converter 130 may arrange the echo signal into a two dimensional (2D) sector-shaped format, or a pyramidal or otherwise shaped three dimensional (3D) format.

The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). The plane data of the multiplanar reformatter 132 may be provided to a volume renderer 134. The volume renderer 134 may generate an image (also referred to as a projection, render, or rendering) of the 3D dataset as viewed from a given reference point, e.g., as described in U.S. Pat. No. 6,530,885 (Entrekin et al.). The volume renderer 134 may generate a render, such as a positive render or a negative render, by any known or future known technique such as surface rendering and maximum intensity rendering.

In some examples, the system may include a Doppler signal path 162 which couples the output from the signal processor 126 to a Doppler processor 160. The Doppler processor 160 may be configured to estimate the Doppler shift and generate Doppler image data. The Doppler image data may include color data which is then overlaid with B-mode (i.e. grayscale) image data for display. The Doppler processor 160 may be configured to filter out unwanted signals (i.e., noise or clutter associated with non-moving tissue), for example using a wall filter. The Doppler processor 160 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function (e.g., ~arg[R1]) and Doppler power estimation is based on the magnitude of the lag-zero autocorrelation function (e.g., R0). The velocity estimations may be referred to as color Doppler data and the power estimations may be referred to as power Doppler data.

Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators.

In some examples, the velocity and power estimates (e.g., the color and power Doppler data) may undergo further threshold detection to further reduce noise, as well as segmentation and post-processing such as filling and smoothing. The velocity and/or power estimates may then be mapped to a desired range of display colors and/or intensities in accordance with one or more color and/or intensity maps. The map data, also referred to as Doppler image data, may then be coupled to the scan converter 130, where the Doppler image data may be converted to the desired image format to form a color Doppler or a power Doppler image.

In some examples, the color Doppler data may include a red-green-blue (RGB) color Doppler image (e.g., a velocity map). The RGB color Doppler image may include a luminance channel and a chrominance channel. The luminance channel may include data corresponding to the intensity (e.g., brightness) of a pixel or voxel of the RGB color Doppler image (e.g., luminance data). The chrominance channel may include data corresponding to the hue (e.g., color) of the pixel or voxel of the RGB color Doppler image (e.g., chrominance data).

According to examples of the present disclosure, the Doppler processor 160 may decompose (e.g., separate) color Doppler data, such as a RGB color Doppler image, into its luminance and chrominance channels. The Doppler processor 160 may adjust (e.g., change) the luminance data based, at least in part, on the power Doppler data. In some examples, the power Doppler data may be used to generate an augmentation map, which may include luminance (e.g., intensity) data in some examples. The augmentation map may be blended with the luminance data of the color Doppler data to generate the adjusted luminance data. The Doppler processor 160 may recombine the chrominance channel and the luminance channel (which now includes the adjusted luminance data) to generate augmented color Doppler data, which may be used to generate an augmented color Doppler image (e.g., an RGB color Doppler image, such as a velocity map). In some examples, the augmented color Doppler image may have improved vascular rendering compared to the original color Doppler image. In some examples, because only the luminance data was changed and the chrominance data was unaltered, quantitative information provided by the color Doppler data may be preserved.

Output (e.g., B-mode images, Doppler images) from the scan converter 130, the multiplanar reformatter 132, and/or the volume renderer 134 may be coupled to an image processor 136 for further enhancement, buffering and temporary storage before being displayed on an image display 138. In some examples, a Doppler image may be overlaid on a B-mode image of the tissue structure by the scan converter 130 and/or image processor 136 for display.

A graphics processor 140 may generate graphic overlays for display with the images. These graphic overlays can contain, for example, standard identifying information such as patient name, date and time of the image, imaging parameters, and the like. For these purposes the graphics processor 140 may be configured to receive input from the user interface 124, such as a typed patient name or other annotations. The user interface 124 can also be coupled to the multiplanar reformatter 132 for selection and control of a display of multiple multiplanar reformatted (MPR) images.

The system 100 may include local memory 142. Local memory 142 may be implemented as any suitable non-transitory computer readable medium (e.g., flash drive, disk drive). Local memory 142 may store data generated by the system 100 including images, maps, executable instructions, inputs provided by a user via the user interface 124, or any other information necessary for the operation of the system 100.

As mentioned previously system 100 includes user interface 124. User interface 124 may include display 138 and control panel 152. The display 138 may include a display device implemented using a variety of known display technologies, such as LCD, LED, OLED, or plasma display technology. In some examples, display 138 may comprise multiple displays. The control panel 152 may be configured to receive user inputs (e.g., blend ratios, saturation level, gain level). The control panel 152 may include one or more hard controls (e.g., buttons, knobs, dials, encoders, mouse, trackball or others). In some examples, the control panel 152 may additionally or alternatively include soft controls (e.g., GUI control elements or simply, GUI controls) provided on a touch sensitive display. In some examples, display 138 may be a touch sensitive display that includes one or more soft controls of the control panel 152.

In some examples, various components shown in FIG. 1 may be combined. For instance, image processor 136 and graphics processor 140 may be implemented as a single processor. In another example, the Doppler processor 160 and B-mode processor 128 may be implemented as a single processor. In some examples, various components shown in FIG. 1 may be implemented as separate components. For example, signal processor 126 may be implemented as separate signal processors for each imaging mode (e.g., B-mode, Doppler). In some examples, one or more of the various processors shown in FIG. 1 may be implemented by general purpose processors and/or microprocessors configured to perform the specified tasks. In some examples, one or more of the various processors may be implemented as application specific circuits. In some examples, one or more of the various processors (e.g., image processor 136) may be implemented with one or more graphical processing units (GPU).

Figure 2:
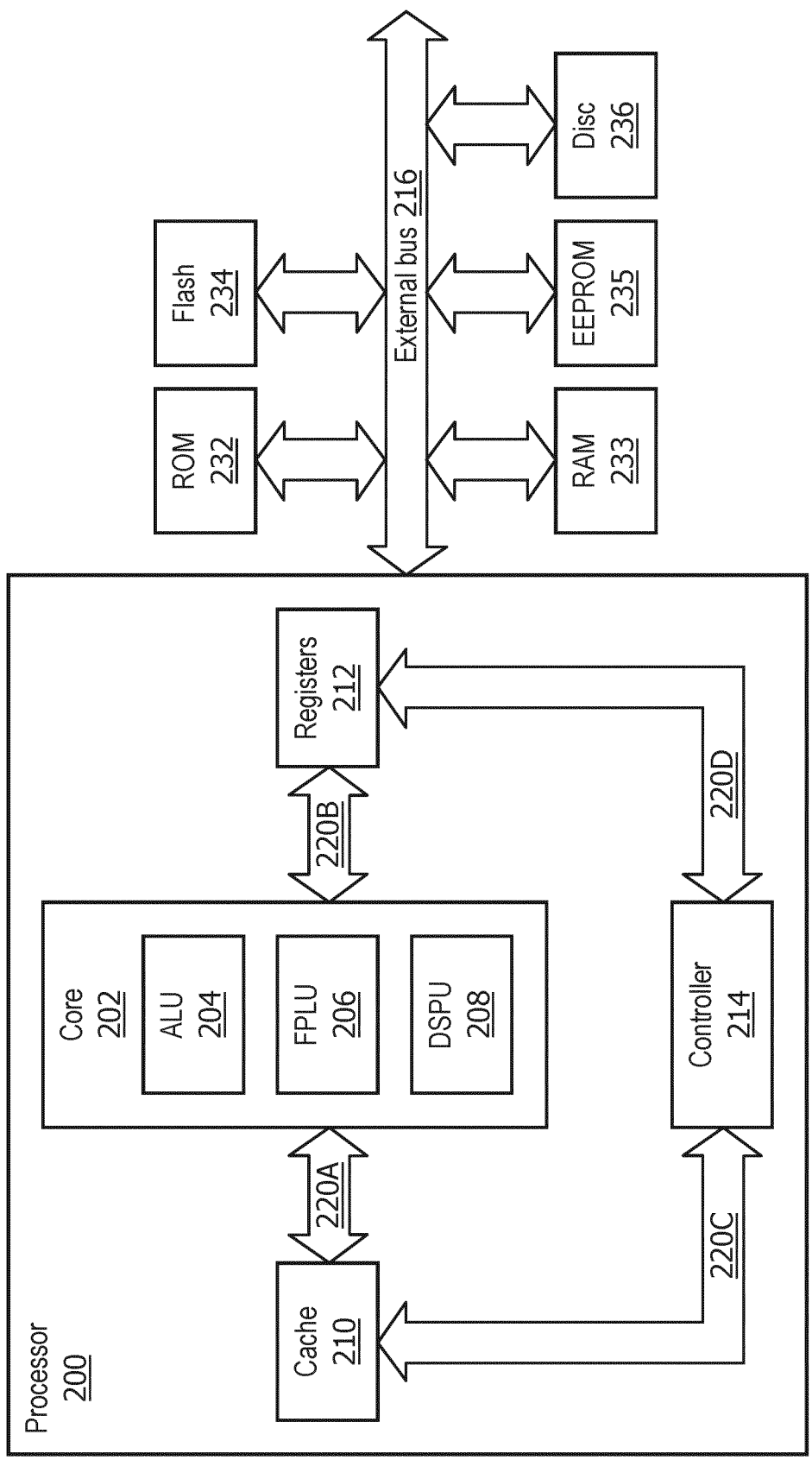
FIG. 2 is a block diagram illustrating an example processor in accordance with examples of the present disclosure.

FIG. 2 is a block diagram illustrating an example processor 200 according to principles of the present disclosure. Processor 200 may be used to implement one or more processors described herein, for example, image processor 136 shown in FIG. 1. Processor 200 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 200 may include one or more cores 202. The core 202 may include one or more arithmetic logic units (ALU) 804. In some examples, the core 202 may include a floating point logic unit (FPLU) 206 and/or a digital signal processing unit (DSPU) 208 in addition to or instead of the ALU 204.

The processor 200 may include one or more registers 212 communicatively coupled to the core 202. The registers 212 may be implemented using dedicated logic gate circuits (e.g., flip-flops) and/or any memory technology. In some examples the registers 212 may be implemented using static memory. The register may provide data, instructions and addresses to the core 202.

In some examples, processor 200 may include one or more levels of cache memory 210 communicatively coupled to the core 202. The cache memory 210 may provide computer-readable instructions to the core 202 for execution. The cache memory 210 may provide data for processing by the core 202. In some examples, the computer-readable instructions may have been provided to the cache memory 210 by a local memory, for example, local memory attached to the external bus 3216. The cache memory 210 may be implemented with any suitable cache memory type, for example, metal-oxide semiconductor (MOS) memory such as static random access memory (SRAM), dynamic random access memory (DRAM), and/or any other suitable memory technology.

The processor 200 may include a controller 214, which may control input to the processor 200 from other processors and/or components included in a system (e.g., control panel 152 and scan converter 130 shown in FIG. 1) and/or outputs from the processor 200 to other processors and/or components included in the system (e.g., display 138 and volume renderer 134 shown in FIG. 1). Controller 214 may control the data paths in the ALU 204, FPLU 206 and/or DSPU 208. Controller 214 may be implemented as one or more state machines, data paths and/or dedicated control logic. The gates of controller 214 may be implemented as standalone gates, FPGA, ASIC or any other suitable technology.

The registers 212 and the cache 210 may communicate with controller 214 and core 202 via internal connections 220A, 220B, 220C and 220D. Internal connections may implemented as a bus, multiplexor, crossbar switch, and/or any other suitable connection technology.

Inputs and outputs for the processor 200 may be provided via a bus 216, which may include one or more conductive lines. The bus 216 may be communicatively coupled to one or more components of processor 200, for example the controller 214, cache 210, and/or register 212. The bus 216 may be coupled to one or more components of the system, such as display 138 and control panel 152 mentioned previously.

The bus 216 may be coupled to one or more external memories. The external memories may include Read Only Memory (ROM) 232. ROM 232 may be a masked ROM, Electronically Programmable Read Only Memory (EPROM) or any other suitable technology. The external memory may include Random Access Memory (RAM) 233. RAM 233 may be a static RAM, battery backed up static RAM, Dynamic RAM (DRAM) or any other suitable technology. The external memory may include Electrically Erasable Programmable Read Only Memory (EEPROM) 235. The external memory may include Flash memory 234. The external memory may include a magnetic storage device such as disc 236. In some examples, the external memories may be included in a system, such as ultrasound imaging system 100 shown in FIG. 1, for example local memory 142.

Figure 3:
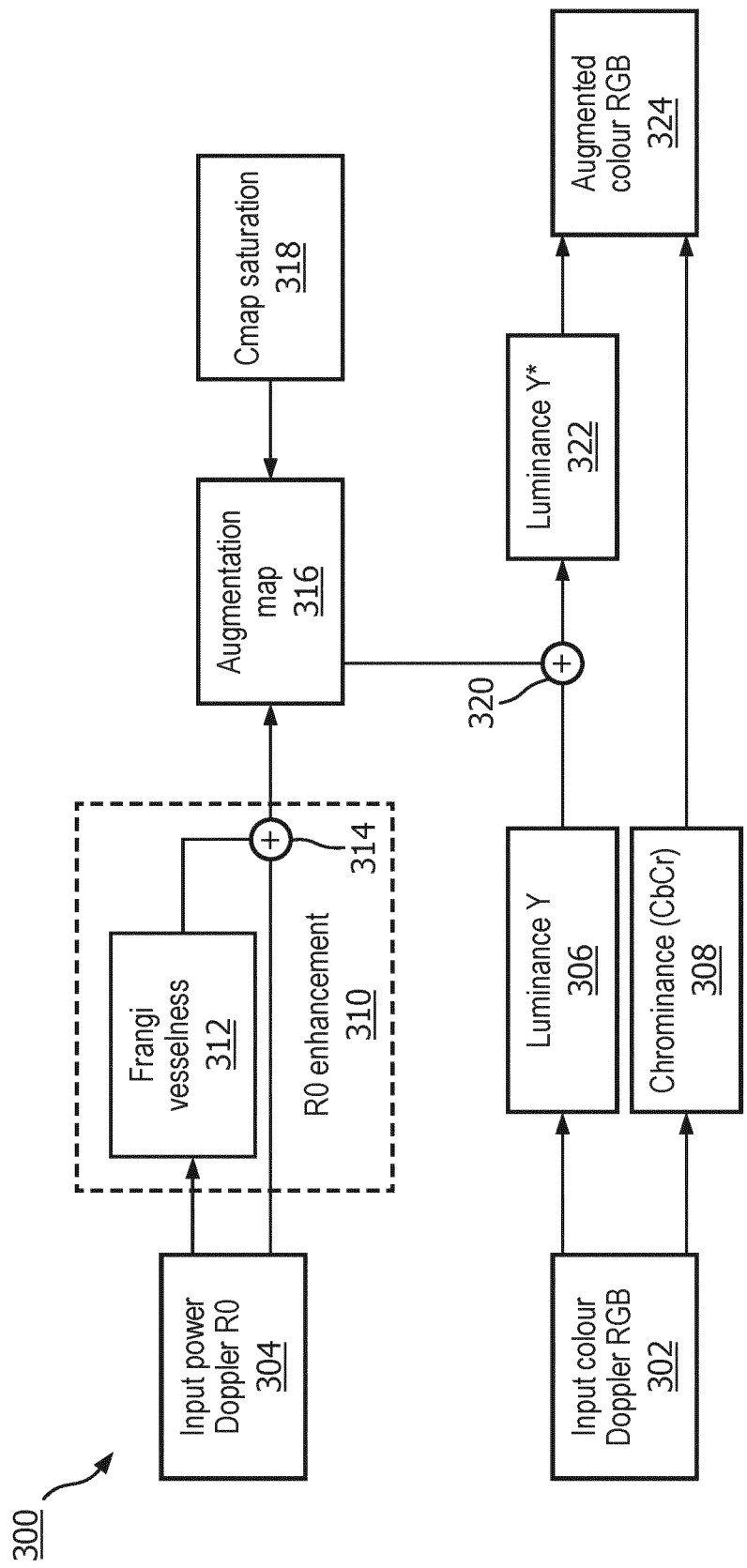
FIG. 3 is a functional block diagram of a portion of a Doppler processor in accordance with examples of the present disclosure.

FIG. 3 is a functional block diagram of a portion of Doppler processor 300 in accordance with examples of the present disclosure. In some examples, the Doppler processor 300 may be included in Doppler processor 160. In some examples, color Doppler data 302 may be provided (e.g., generated by a velocity estimator in another portion of the Doppler processor 300 as described with reference to FIG. 1). The color Doppler data 302 may include an RGB image (e.g., an RGB color Doppler image). In some examples, the RGB image may include a velocity map. In some examples, power Doppler data 304 may be provided (e.g., generated by a power estimator in another portion of the Doppler processor 300 as described with reference to FIG. 1).

The Doppler processor 300 may decompose the color Doppler data 302 into its luminance channel (luminance data 306) and chrominance channel (chrominance data 308) components. In other words, the color Doppler data 302 is re-expressed in a color space that separates image brightness from chroma (e.g., hue). Multiple techniques for decomposing the Doppler data 302 may be used to obtain the luminance data 306 and the chrominance data 308, such as YCbCr, HSV, or CIE L*A*B. For illustrative purposes, the YCbCr technique will be provided as an example. However, the disclosure is not limited to this technique.

The YCbCr technique includes an approximation of color processing and perceptual homogeneity and may be estimated by the following linear transformations:

$$\begin{pmatrix} Y \\ Cb \\ Cr \end{pmatrix} = \begin{pmatrix} 65.5 & 128.5 & 25 \\ -37.8 & -74.2 & 112 \\ 112 & -93.8 & -18.2 \end{pmatrix} \begin{pmatrix} R \\ G \\ B \end{pmatrix} + \begin{pmatrix} 16 \\ 128 \\ 128 \end{pmatrix} \qquad \text{Equation 1}$$

Where Y is the luminance (e.g., brightness information), Cb is the blue chroma, Cr is the red chroma, and R, G, and B are the inputs of the original color Doppler data 302 (e.g., the RGB image). The Y obtained by Equation 1 is the luminance data 306 and the CbCr obtained by Equation 1 is the chrominance data 308. Decomposing the color Doppler data 302 into the luminance data 306 and the chrominance data 308 allows modification of either the luminance data 306 and/or the chrominance data 308 without affecting the other. That is, the data of the luminance channel and the chrominance channel may be adjusted independently.

The power Doppler data 304 may be used to generate an augmentation map 316. The augmentation map 316 may include brightness information (e.g., luminance), which in some examples may correspond to volume of flow. That is, brighter pixels may correspond to larger volumes of blood flowing at a location corresponding to that pixel than at locations corresponding to darker pixels. In some examples, the power Doppler data 304 may be encoded into a dynamic range to generate the augmentation map 316. For example, the dynamic range may be [0,1], where the encoded luminance values of the augmentation map 316 may have a minimum value of 0 and a maximum value of 1. In some examples, the noise floor may be set to 0 and max[R0] may be set to 1. In some examples, a gamma compression may be applied. Proto-code for encoding and compressing the data is provided below:

normR0data=(R0−NoiseR0)/max(R0−NoiseR0);
normR0data(normR0data<0)=0;  normR0data (normR0data>1)=1;
AugR0=normR0data.^(gamma); % gamma compression Optionally, after encoding, the power Doppler data 304 (now AugR0) may be further processed to provide enhanced Doppler data 310 to generate the augmentation map 316. In some examples, advanced imaging filters may be applied to power Doppler Data 304 AugR0 (e.g., Xres, bilateral filters, etc.) in order to denoise speckle, improve edge sharpness, and/or improve contrast.

In some examples, the principle curvature of R0 of the power Doppler Data 304 may be extracted from power Doppler Data 304 AugR0, which may improve rendering of tubular structures such as blood vessels. In some examples, a Frangi vesselness filter 312 may be applied to extract the principle curvature. In some examples, the principle curvature includes the second derivative computed perpendicularly to a blood vessel and is estimated from eigenvalues of a Hessian matrix. An example of this Frangi vesselness filter may be found in Frangi A. F., Niessen W. J., Vincken K. L., Viergever M. A. (1998) *Multiscale vessel enhancement filtering*. In: Wells W. M., Colchester A., Delp S. (eds) *Medical Image Computing and Computer-Assisted Intervention*—MICCAI'98. MICCAI 1998. Lecture Notes in Computer Science, vol. 1496. Springer, Berlin, Heidelberg. However, other tubular and/or morphological filters and/or techniques may be applied. For example, a filter designed to isolate blood pool-like structures may be used in place of Frangi vesselness filter 312. In another example, a despeckling filter, a bilateral filter, and/or a non-local mean filter may be used in place of the Frangi vesselness filter.

In some examples, the output of the Frangi vesselness filter 312 may be used to generate the augmentation map 316. In other examples, the output of the Frangi vesselness filter 312 may be blended with the power Doppler data 304 AugR0 (which may be the originally encoded data or data processed by additional filters as discussed above) by combiner 314. The blending may be described by the formula:

$$Aug=Aug_{R0}(1-\alpha)+Aug_{Frangi}\alpha \qquad \text{Equation 2}$$

Where Aug is the resulting augmentation map 316, AugR0 is the power Doppler data 304, $Aug_{Frangi}$ is the output of the Frangi vesselness filter 312, and α is the blending factor.

The resulting augmentation map 316 may be combined with the luminance data 306 by combiner 320 to generate the adjusted luminance data 322. In some examples, the combiner 320 may blend the augmentation map 316 and the luminance data 306 according to the following formula:

$$Y^*=Y(1-\beta)+Aug(\beta+saturation) \qquad \text{Equation 3}$$

Where Y* is the adjusted luminance data 322, Y is the original luminance data 306, Aug is the augmentation map 316, and β is the blending factor. When β=0, Equation 3 yields the original luminance data 306 as Y* and β=1 allows the augmentation map 316 to have the maximum effect the resulting adjusted luminance data 322. Optionally, a saturation bias may be included, shown as "saturation" in Equation 3. In some applications, the saturation bias may saturate the luminance to improve contrast. In some examples, the saturation bias may have a value from 0-1 (inclusive). As shown in FIG. 3, in addition to or instead of the saturation bias in Equation 3, a saturation factor 318 (e.g., a Cmap saturation) may be applied to the augmentation map 316 prior to combining with the luminance data 306.

The adjusted luminance data 322 may be recombined with the original chrominance data 308 to generate the augmented color Doppler data 324. As mentioned previously, the augmented color Doppler data 324 may include a color (e.g., RGB) velocity map. The luminance channel and chrominance channel may be recombined by performing an inverse of the operation used to decompose the channels. In the YCbCr example provided, the inverse of Equation 1 would be used to obtain the RGB data. In some examples, the augmented color Doppler data 324 may be provided from the Doppler processor 300 to a scan converter (such as scan converter 130) and/or image processor (such as image processor 136). The augmented color Doppler data 324 may be used to generate a color Doppler image, such as a velocity color map, for display on a display (such as display 138). In some examples, the augmented color Doppler image may be overlaid on a B-mode image.

In some examples, at least some of the inputs of Equations 1-3 may be defined by a user input received through a user interface (such as user interface 124). For example, the degree of blending performed by combiner 314 and/or combiner 320 may be determined by a user input (e.g., β and/or α). In another example, the saturation bias may be determined by a user input. In some examples, whether or not and/or how the power Doppler data is enhanced may be based, at least in part, on a user input (e.g., whether or not Frangi vesselness filter 312 is used).

Figure 4:
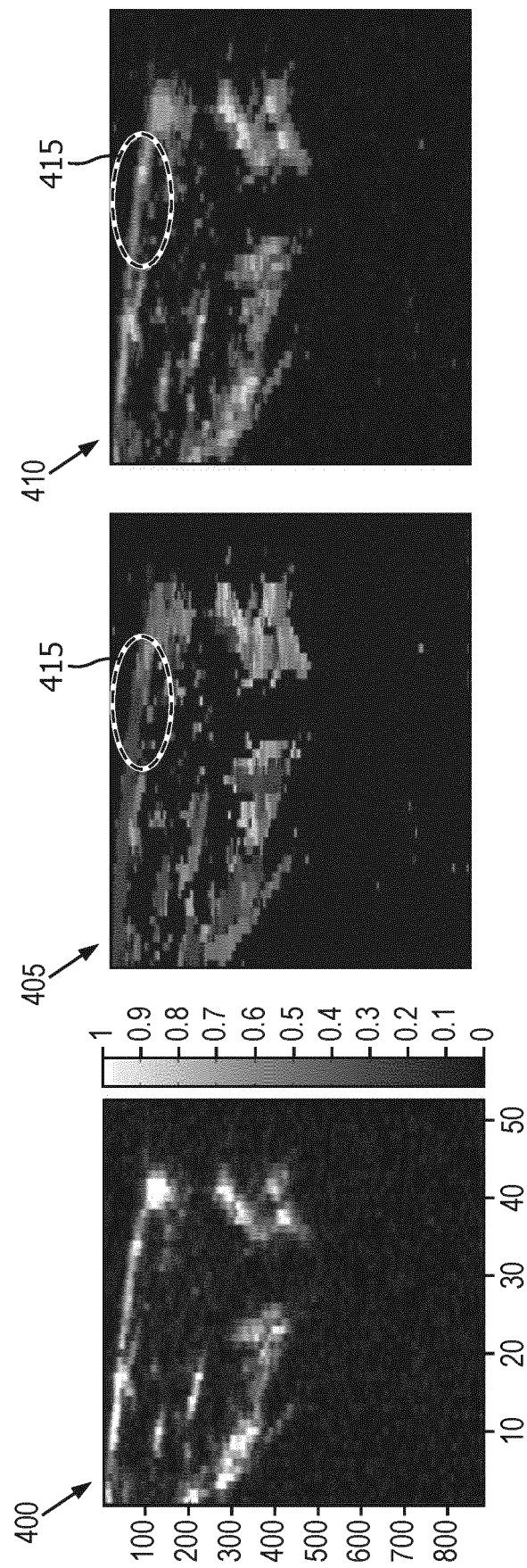
FIG. 4 shows an example augmentation map, a color Doppler velocity map, and an augmented color Doppler velocity map in accordance with examples of the present disclosure.

FIG. 4 shows an example augmentation map 400, a color Doppler velocity map 405, and an augmented color Doppler velocity map 410 in accordance with examples of the present disclosure. The images were generated from ultrasound data acquired from imaging a human thyroid. The augmentation map 400 was computed from R0 power Doppler data that was enhanced by a Frangi vesselness filter as described with reference to FIG. 3. The color Doppler velocity map 405 was generated from the original color Doppler data (e.g., ~arg[R1]). The color Doppler data of the color Doppler velocity map 405 was decomposed into its luminance and chrominance channels using the YCbCr technique as described with reference to FIG. 3. The luminance data was then adjusted by the augmentation map 400 by blending using Equation 3, where β=0.7 and saturation=0.15. The adjusted luminance data was recombined with the chrominance data to generate the augmented color Doppler data. The augmented color Doppler data is shown as the augmented color Doppler velocity map 410. As can be seen, for example in circled region 415, the augmented color Doppler velocity map 410 has improved rendering of vasculature compared to the original color Doppler velocity map 405.

Figure 5:
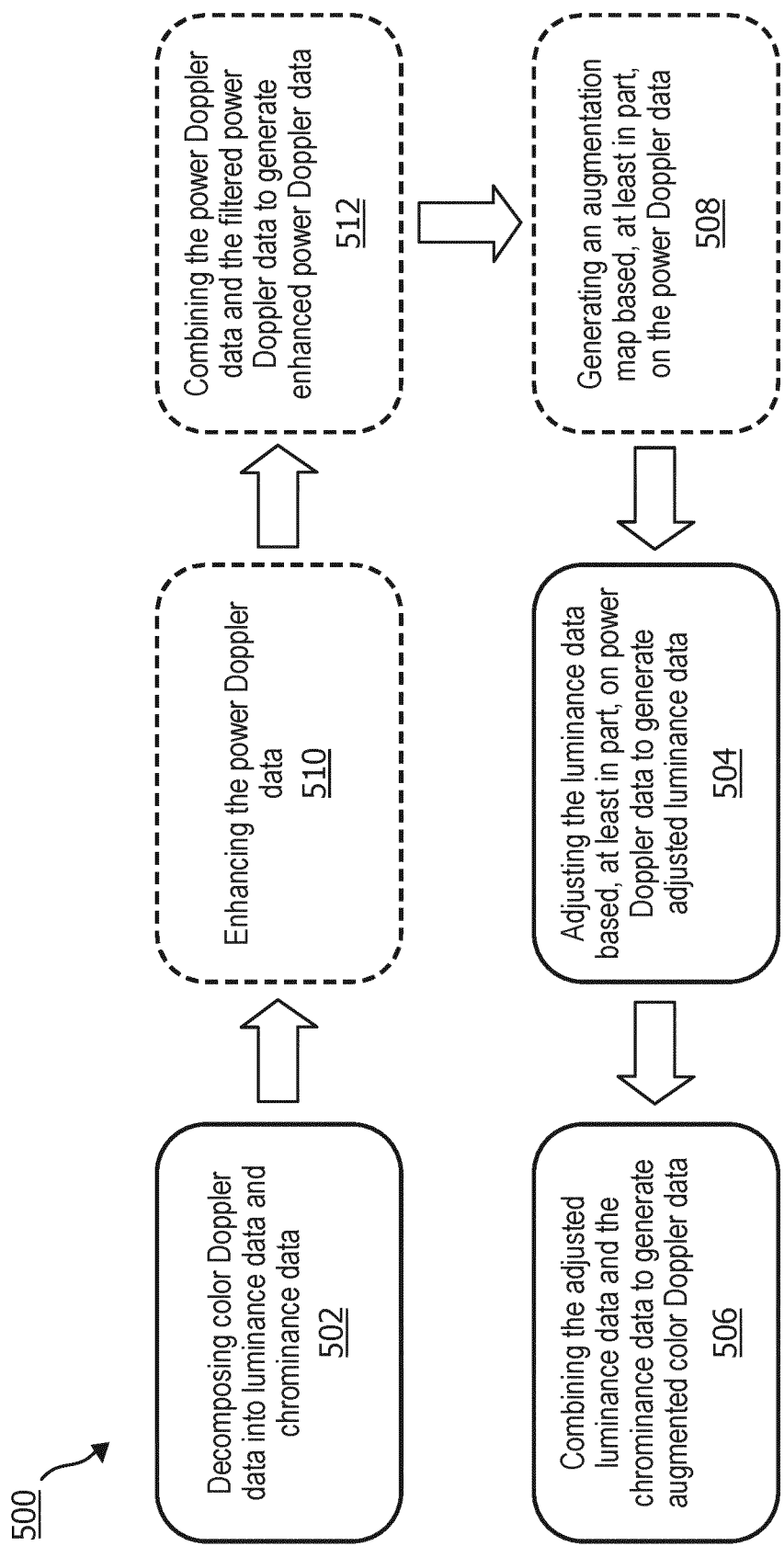
FIG. 5 is a flow chart of a method according to principles of the present disclosure.

FIG. 5 is a flow chart of a method 500 according to principles of the present disclosure. In some examples, at least a portion of the method 500 may be performed by ultrasound imaging system 100 and/or Doppler processor 300.

At block 502, "decomposing color Doppler data into luminance data and chrominance data" may be performed. In some examples, the color Doppler data may be decomposed by using the YCbCr technique. In other examples, other techniques may be used (e.g., HSV). The decomposing may be performed by a Doppler processor, such as Doppler processor 160 and/or Doppler processor 300, in some examples.

At block 504, "adjusting the luminance data based, at least in part, on power Doppler data to generate adjusted luminance data" may be performed.

At block 506, "combining the adjusted luminance data and the chrominance data to generate augmented color Doppler data" may be performed. In some examples, the adjusted luminance data and the chrominance data may be combined using an inverse of the technique used at block 502. For example, an inverse of the YCbCr technique may be used.

In some examples, prior to block 504, at block 508, "generating an augmentation map based, at least in part, on the power Doppler data" may be performed. In these examples, adjusting the luminance data may include combining the augmentation map and the luminance data. In some examples, combining the augmentation map and the luminance data may include blending the augmentation map and the luminance data based, at least in part, on a blending factor. In some examples, the blending factor may be determined by a user input. In some examples, the user input may be received from a user interface, such as user interface 124. In some examples, combining the augmentation map and the luminance data may include applying a saturation bias.

In some examples, generating the augmentation map may include encoding the power Doppler data, for example encoding the power Doppler data into a [0,1] dynamic range. In some examples, generating the augmentation map may include applying a gamma compression to the power Doppler data.

In some examples, prior to block 508, "enhancing the power Doppler data" may be performed at block 510. In some examples, the power Doppler data may be enhanced by applying a filter to generate filtered power Doppler data. In some examples, the filter may be a Frangi vesselness filter (e.g., Frangi vesselness filter 312). In some examples, after block 510 and prior to block 508, "combining the power Doppler data and the filtered power Doppler data to generate enhanced power Doppler data" may be performed at block 512. In these examples, the enhanced power Doppler data may be used to generate the augmentation map.

In some examples, generating a velocity color map based on the augmented color Doppler data may be performed after block 506. In some examples, the velocity color map may be overlaid on a B-mode image. In some examples, these actions may be performed by a scan converter (e.g., scan converter 130) and/or an image processor (e.g., image processor 136). The velocity color map and/or B-mode image may be provided on a display, such as display 138 in some examples.

The systems and methods described herein may decompose color Doppler data into a luminance channel and a chrominance channel. The data of the luminance channel may be adjusted based, at least in part, on power Doppler data while the chrominance data remains unaltered. The adjusted data of the luminance channel may be recombined with the unaltered data of the chrominance channel to provide augmented color Doppler data. In some applications, the augmented color Doppler data may provide improved rendering of vessels, for example, in a color velocity map. In some applications, the quantitative data regarding blood flow of the color Doppler data may be preserved.

In various examples where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, examples or processes described herein may be combined with one or more other examples, examples and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular example or group of examples. Thus, while the present system has been described in particular detail with reference to exemplary examples, it should also be appreciated that numerous modifications and alternative examples may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. An ultrasound imaging system comprising:
    a processor configured to:
        analyze ultrasound signals to generate power Doppler data and color Doppler data;
        separate the color Doppler data into luminance data and chrominance data;
        adjust the luminance data based, at least in part, on the power Doppler data to generate adjusted luminance data; and
        combine the adjusted luminance data and the chrominance data to generate augmented color Doppler data.

2. The ultrasound imaging system of claim 1, wherein the processor is further configured to enhance the power Doppler data based, at least in part, on applying a filter to the power Doppler data.

3. The ultrasound imaging system of claim 2, wherein the filter is a morphological filter.

4. The ultrasound imaging system of claim 1, further comprising a user interface configured to receive a user input, wherein the user input defines, at least in part, how the luminance data is adjusted by the power Doppler data.

5. The ultrasound imaging system of claim 4, wherein the user input defines a blending factor to blend the luminance data and the power Doppler data to generate the adjusted luminance data.

6. A method comprising:
    decomposing color Doppler data into luminance data and chrominance data;
    adjusting the luminance data based, at least in part, on power Doppler data to generate adjusted luminance data; and
    combining the adjusted luminance data and the chrominance data to generate augmented color Doppler data.

7. The method of claim 6, wherein the color Doppler data is decomposed using a first technique and the adjusted luminance data and the chrominance data are combined using an inverse of the first technique.

8. The method of claim 6, further comprising:
    generating an augmentation map based, at least in part, on the power Doppler data, wherein adjusting the luminance data comprises combining the augmentation map and the luminance data.

9. The method of claim 8, wherein generating the augmentation map includes encoding the power Doppler data into a dynamic range.

10. The method of claim 9, wherein generating the augmentation map includes applying a gamma compression to the power Doppler data.

11. The method of claim 8, further comprising enhancing the power Doppler data by applying a filter to generate filtered power Doppler data.

12. The method of claim 11, wherein the filter is a morphological filter.

13. The method of claim 11, further comprising combining the power Doppler data and the filtered power Doppler data to generate enhanced power Doppler data, wherein the enhanced power Doppler data is used to generate the augmentation map.

14. The method of claim 8, wherein combining the augmentation map and the luminance data comprises blending the augmentation map and the luminance data based, at least in part, on a blending factor.

15. The method of claim 14, wherein the blending factor is determined by a user input received from a user interface.

16. The method of claim 8, wherein combining the augmentation map and the luminance data further comprises applying a saturation bias.

17. The method of claim 6, further comprising:
    generating a velocity color map based on the augmented color Doppler data; and
    overlaying the velocity color map on a B-mode image.

18. A non-transitory computer readable medium including instructions, that when executed, cause an ultrasound imaging system to:
    analyze ultrasound signals to generate power Doppler data and color Doppler data;
    separate the color Doppler data into luminance data and chrominance data;
    adjust the luminance data based, at least in part, on the power Doppler data to generate adjusted luminance data; and
    combine the adjusted luminance data and the chrominance data to generate augmented color Doppler data.

19. The non-transitory computer readable medium of claim 18, further including instructions, that when executed, cause the ultrasound imaging system to:
    enhance the power Doppler data by applying at least one filter to the power Doppler data to generate enhanced power Doppler data;
    generate an augmentation map based, at least in part, on the enhanced power Doppler data; and
    blend the augmentation map and the luminance data to generate the adjusted luminance data.

20. The non-transitory computer readable medium of claim 18, further including instructions, that when executed, cause the ultrasound imaging system to generate and display a velocity color map from the augmented color Doppler data.

\* \* \* \* \*